(12) United States Patent
Solanki et al.

(10) Patent No.: US 12,268,416 B2
(45) Date of Patent: Apr. 8, 2025

(54) PERCUTANEOUS CATHETER SYSTEM FOR IMPLANT DELIVERY

(71) Applicant: SAHAJANAND MEDICAL TECHNOLOGIES LIMITED, Gujarat (IN)

(72) Inventors: Chirag Maheshbhai Solanki, Gujarat (IN); Abhijeet Singhvi, Gujarat (IN); Shivanshu Pandey, Uttar Pradesh (IN)

(73) Assignee: SAHAJANAND MEDICAL TECHNOLOGIES LIMITED, Gujarat (IN)

( * ) Notice: Subject to any disclaimer, the term of this patent is extended or adjusted under 35 U.S.C. 154(b) by 358 days.

(21) Appl. No.: 17/816,664

(22) Filed: Aug. 1, 2022

(65) Prior Publication Data
US 2023/0371980 A1 Nov. 23, 2023

Related U.S. Application Data

(63) Continuation of application No. PCT/IN2022/050607, filed on Jul. 1, 2022.

(30) Foreign Application Priority Data

May 17, 2022 (IN) .............................. 202221028378

(51) Int. Cl.
*A61B 17/34* (2006.01)
*A61B 17/00* (2006.01)
*A61M 25/00* (2006.01)
*A61M 25/01* (2006.01)
*A61M 25/09* (2006.01)

(52) U.S. Cl.
CPC ..... *A61B 17/3468* (2013.01); *A61B 2017/00292* (2013.01); *A61M 2025/0004* (2013.01); *A61M 25/0108* (2013.01); *A61M 25/0136* (2013.01); *A61M 25/09* (2013.01)

(58) Field of Classification Search
CPC ............ A61B 17/3468; A61B 17/1205; A61B 2017/9517; A61B 2017/00367; A61B 2017/00623; A61M 25/0136; A61M 25/09; A61M 2025/0004–0006; A61M 25/0097;
(Continued)

(56) References Cited

U.S. PATENT DOCUMENTS

2011/0251683 A1* 10/2011 Tabor ................... A61F 2/2436
623/2.11
2017/0056169 A1 3/2017 Johnson et al.

OTHER PUBLICATIONS

International Search Report for Application No. PCT/IN2022/050607, three pages, dated Feb. 6, 2023.
(Continued)

*Primary Examiner* — Katherine H Schwiker
*Assistant Examiner* — Lauren Dubose
(74) *Attorney, Agent, or Firm* — Nixon & Vanderhye P.C.

(57) ABSTRACT

A catheter system for implant delivery is provided. The delivery system includes a primary rotary knob and a secondary rotary knob. The primary rotary knob moves a catheter shaft to load or unload an implant whereas the secondary rotary knob is connected to an inner shaft. The inner shaft comprises an implant holder to engage with the implant during loading and unloading. The movement of the inner shaft due to rotation of the secondary rotary knob improves positioning of the implant and ensures detachment of the implant from the implant holder due to micro movements of the implant holder.

14 Claims, 3 Drawing Sheets

(58) Field of Classification Search
CPC ...... A61F 2/966; A61F 2/9517; A61F 2/2436; A61F 2/011
See application file for complete search history.

(56) References Cited

OTHER PUBLICATIONS

Written Opinion of the ISA for Application No. PCT/IN2022/050607, five pages, dated Feb. 6, 2023.

\* cited by examiner

PERCUTANEOUS CATHETER SYSTEM FOR IMPLANT DELIVERY

CROSS REFERENCE(S) TO RELATED APPLICATIONS

This application is a continuation of PCT application No. PCT/IN2022/050607, filed Jul. 1, 2022, which claims priority to Indian Application No. 202221028378, filed May 17, 2022, the entire contents of each being hereby incorporated by reference.

TECHNICAL FIELD

The present invention relates to an implant delivery system and method to position and deliver an implant using a percutaneous catheter system for implant delivery.

BACKGROUND

A healthy heart along with healthy arteries, veins, valves, nodes, walls, and remaining constituents, is essential for proper functioning of the other organs and the cardiovascular system itself. However, due to factors like age, disease, infections or genetic disorder, the working efficiency of the cardiovascular system reduces significantly and that is a severe and potentially life-threatening condition. Conventionally, surgery was one main option to address the severely diseased organ or its part e.g., replacing the diseased organ or its part by a mechanical implant or by bypassing the diseased organ or its part or by removing the diseased organ or its part using a harvested organ or its part. However, in recent years, an alternative less invasive transcatheter approach has been developed that delivers an implant using a percutaneous catheter that can be navigated to the targeted location transvascularly through variety of access points in a vascular network e.g., through femoral artery, transapically, transaortic, trans-axillary etc. These implants may be, but not limited to, a stent, a valve, a mesh, a balloon, a patch, a drug-containing matrix, a shunt, or a combination thereof.

During a transvascular procedure, a catheter system for implant delivery, carrying an implant, plays a vital role as the operator's maneuvering actions at proximal end (handle) of the delivery system directly impacts the positioning, movement of the distal section (tip and capsule), and performance of the implant after the deployment. The effect of maneuvering actions transfers through a catheter shaft from the proximal end to the distal end. The catheter shaft is situated between the proximal end and the distal end. However, sometimes, the implant doesn't get detached from the delivery system quickly and requires additional maneuvering that increases time required for completing the medical procedure and, often, reduces accuracy in positioning of the implant.

Hence, there is a need to provide a catheter system for implant delivery for transvascularly delivering implants that can avoid the shortcomings known in the art. For example, to specifically provide a catheter system for implant delivery that provides improved positioning of the implant and ensures detachment of the implant. In addition, the catheter system for implant delivery should be ergonomic in use and has sturdy structural design. Another objective of is to provide an catheter system for implant delivery that has better implant detachment by providing a movable implant holder.

SUMMARY

The subject matter is illustrated, according to various aspects described below.

According to an aspect, a percutaneous catheter for delivery of an implant, comprises a primary rotary knob connected with a catheter shaft to cause longitudinal movement of the catheter shaft. A secondary rotary knob connected with an inner shaft to cause longitudinal movement of the inner shaft wherein the secondary rotary knob is connected to a threaded wheel and the threaded wheel is engaged with the secondary rotary knob through threads. An eccentric luer having a guidewire port connected to a guidewire shaft. At least one luer arm connected to the eccentric luer and situated at a distance in radial direction wherein the luer arm is parallel to the longitudinal axis passes through the center of the guidewire port and the guidewire shaft. At least a groove cut in the threaded wheel in the longitudinal direction and accessible from at least one cross-sectional surface of the threaded wheel. The luer arm passes through the groove in the thread wheel and the threaded wheel moves in longitudinal direction over the luer arm on rotary motion of the secondary rotary knob.

It will be appreciated that the above-described features are merely examples and other features, aspects, and advantages of the subject matter are further illustrated in the figures and described in the corresponding description below.

BRIEF DESCRIPTION OF ACCOMPANYING DRAWINGS

The detailed description is described with reference to the accompanying figures.

DETAILED DESCRIPTION

Figure 1:
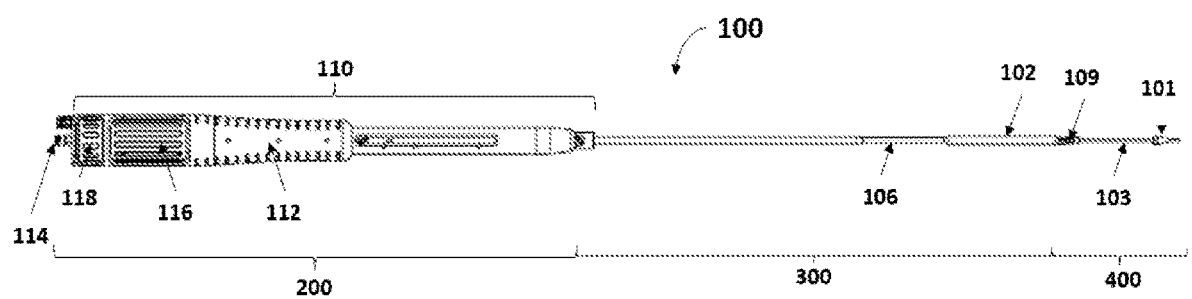
FIG. 1 illustrates a side view of a transcatheter system for implant delivery where a capsule is in retracted position, according to certain example embodiments.

Present disclosure provides an embodiment of a catheter system for implant delivery, specifically a catheter for transvascularly delivering and deploying an implant in a living entity e.g. human body or animal body. The catheter comprises a distal section, a middle section, and a proximal section. The proximal section remains outside the living entity and comprises a handle that encompasses mechanisms to control the movements at the distal section of the catheter. The distal section comprises, an implant holder, a tip and a capsule assembly wherein, in a loaded state, the capsule assembly comprises an implant on a guidewire shaft. The middle section is connected proximally with the handle and distally it connects to the distal section.

The middle section is situated between the handle and the capsule assembly. The middle section comprises a plurality of concentric shafts where all the shafts are at least present over one fourth of the total length of the middle section. The middle section at least has the guidewire shaft, an inner shaft, and a catheter shaft. The guidewire shaft is the innermost shaft and goes through the inner shaft concentrically. The guidewire shaft start from a proximal-most side of the proximal section and goes till a distal-most side of the distal section. The inner shaft starts from a proximal-most side of the proximal section and goes till start of the distal section or where the capsule starts in complete forwarded state. The inner shaft goes through the catheter shaft concentrically. Hence, over the length of the middle section at a point where at least abovementioned three shafts are present, cross sectionally and from the center, the order of the shafts is the guidewire shaft, the inner shaft and the catheter shaft where all the shafts have a common center point.

The proximal section comprises the handle that comprises a primary rotary knob, a secondary rotary knob wherein the secondary rotary knob is connected to a threaded wheel and the threaded wheel is engaged with an eccentric luer. The primary rotary knob is connected to a screw-based mechanism for causing movement at the distal section and specifically for moving the capsule that is distal part of the catheter shaft. Rotary movement of the secondary rotary knob causes movement of the inner shaft in longitudinal direction whereas the guidewire shaft is fixed to the eccentric luer and remains stationary. Both, the primary rotary knob and the secondary rotary knob, are situated in a handle housing. The handle housing is also part of the handle and provides protection to the mechanisms causing movement and also provides grip to the user.

The secondary rotary knob is fixed in the handle housing and cannot move longitudinally. Also, the secondary rotary knob is a cylindrical structure that has threads on its inner periphery. Through these inner threads, the secondary rotary knob is engaged with the threaded wheel. The threaded wheel is also of cylindrical structure with threads on its outer periphery. The threaded wheel also has a narrow hole in its center. The diameter of the narrow hole is larger than the outer diameter of the inner shaft. The proximal end of the inner shaft is connected with the narrow hole. Hence, on rotation of the secondary rotary knob, the threaded wheel moves in longitudinal direction either towards the tip or in opposite direction depending on the direction of the rotation of the secondary rotary knob. As above mentioned, the inner shaft is connected with the threaded wheel. Hence, on longitudinal movement of the threaded wheel, the inner shaft also moves accordingly in longitudinal direction.

Further, the threaded wheel has at least one groove cut in longitudinal direction. The groove is accessible from at least one cross-sectional surface of the threaded wheel. According to one embodiment of the present disclosure, in circumferential direction, the width of the groove is variable and at the upper limit, the width can be wide enough till the threaded wheel does not lose its ability to move in longitudinal direction due to rotary movement of the secondary rotary knob.

In addition, the threaded wheel is engaged to the eccentric luer through the groove. The eccentric luer has at least one guidewire port and at least one luer arm wherein the guidewire port is aligned to the center of the threaded wheel. However, the luer arm is attached to the luer in such a way so that the longitudinal axis of the luer arm is parallel to the longitudinal axis going through the center of the guidewire port and the narrow hole but the longitudinal axis of the luer arm is situated at a distance in radial direction from the longitudinal axis going through the center of narrow hole. The eccentric luer is engaged to the groove through the luer arm. The luer arm also functions as a guiderail for the threaded wheel and the length of the luer arm is sufficient to provide support to the threaded wheel while it moves in longitudinal direction. On assembling the parts, the eccentric luer does not move and the engagement of the luer arm with the grove restricts the rotational movement of the threaded wheel. Hence, on rotation of the secondary rotary knob, the threaded wheel only moves in longitudinal direction.

Further, the guidewire port of the eccentric luer is connected with the guidewire shaft. The guidewire shaft is also hollow and as explained above, extends from the guidewire port situated at the proximal-most side of the proximal section till a distal-most part of the tip. The hollow guidewire shaft provides an access path for a guidewire during the medical procedure. The guidewire shaft is fixed to the catheter system for implant delivery and does not move longitudinally.

Further, as per another embodiment, to lock the movement of the secondary rotary knob a safety mechanism is provided. The safety mechanism comprises a safety pin and a safety slot, when engaged, lock the movement of the secondary rotary knob. The safety slot can be designed on the peripheral surface or on the cross-sectional of the secondary rotary knob or the safety slot can also be present as a protrusion on any surface of the secondary rotary knob. The safety pin can be removable from the handle or can be attached to the handle and communicable with the safety slot in either engaged state or in disengaged state.

According to an embodiment of the present disclosure, the safety pin is a removable pin and the safety slot is a hole on the cross-sectional surface of the secondary rotary knob. On inserting the safety pin in the safety slot, the rotational movement of the secondary rotary knob restricts and that results in restricted longitudinal movement of the inner shaft.

The catheter system for implant delivery as per an embodiment of the present disclosure utilizes two movement mechanisms for loading, positioning, and deployment of the prosthetic heart valve. The catheter shaft is connected to the primary rotary knob and on rotating the primary rotary knob, the catheter shaft moves in on its longitudinal axis. The catheter shaft's backward or forward movement depends on the direction of the rotation of the primary rotary knob. The distal end of the catheter shaft has the capsule where the implant is loaded on the guidewire shaft in compressed form. Backward movement of the catheter shaft causes backward movement of the capsule that releases the implant for deployment. The inner shaft is attached to the implant holder and the implant holder is engaged with the implant during loading of the implant in the capsule and it remains engaged until backward movement of the capsule releases the implant for deployment. The inner shaft moves in longitudinal axis on rotating the secondary rotary knob. The longitudinal movement of the inner shaft causes longitudinal movement of the implant holder. The movement of the implant holder ensures detachment of the implant from the catheter system for implant delivery.

According to yet another embodiment of the present disclosure, the implant may be, but not limited to, a stent, a valve, a mesh, a balloon, a patch, a drug-containing matrix, a shunt, or a combination thereof.

According to yet another embodiment of the present disclosure, the inner shaft is connected to the narrow hole through adhesive, sealant, glue, threads, welding or other mechanical, chemical or combination of both type of connecting measures known in the art.

According to yet another embodiment of the present disclosure, at least an additional element can be placed between the guidewire shaft and the inner periphery of the guidewire port to strengthen the connection between the guidewire port and the guidewire shaft. Similar elements can also be placed between the inner shaft and the inner periphery of the narrow hole to strengthen the connection between them. The additional element may be made of a metal, non-metal, alloy, polymer, wood, natural fiber, synthetic fiber or a combination thereof. Physical form of the additional element is selected from a hollow circular ring, a hollow cylinder, a ring whose periphery, inner or outer, has at least one angle, a ring whose periphery, inner or outer, has threads, a ring whose periphery, inner or outer, has at least one barb or a combination thereof.

According to yet another embodiment of the present disclosure, the safety mechanism can be of various configurations, specifically selected from, but not limited to, threaded type, hook type, lock-pin type, switch type (on/off type), Velcro-based, magnetic type or a combination thereof.

According to yet another embodiment of the present disclosure, the catheter system for implant delivery comprises an indicating mechanism to show the extent of the implant delivery, during the implant delivery procedure.

According to yet another embodiment of the present disclosure, the catheter system for implant delivery comprises at least a radiopaque marker on its distal section including the tip, the guidewire shaft, the capsule and the inner shaft to indicate the location of the particular element of the loaded implant once the implant is inside the human or animal body.

According to yet another embodiment, the implant has at least one design element that can be engaged with the pin. Such design element may be, but not limited to, a hook-shaped element, a ring-shaped element, a closed ring-shaped element, an open ring-shaped element, an irregular-close-shaped element, an irregular-open-shaped element, a U-shaped element, a V-shaped element, a W-shaped element, a M-shaped element, an end part of a stent, a valve or a shunt that can be put around the pin, part of a mesh, part of a frame, or a combination thereof.

According to yet another embodiment, the implant is used in treating any abnormality or in any medical procedure related to heart, kidney, lever, brain, pancreas, lungs, digestive system, endovascular system, any tract, duct or any conduit in animal or human body. More specifically, the implant can be deployed in an artery, vein, heart valves, esophageal duct, bile duct, urinary tract, alimentary tract, tracheobronchial tree, cerebral aqueduct or genitourinary system of an animal or human body.

By combining different materials and design variations explained above, a variety of configurations can be obtained with varying structure-property relationships.

Now, referring to the figures, wherein the elements are labelled with like numerals throughout the several Figures. Further, reference is made to the accompanying drawings which form a part hereof, and in which is shown by way of illustration. It is to be understood that other embodiments may be utilized, and structural changes may be made without departing from the scope of the invention.

Figure 1A:
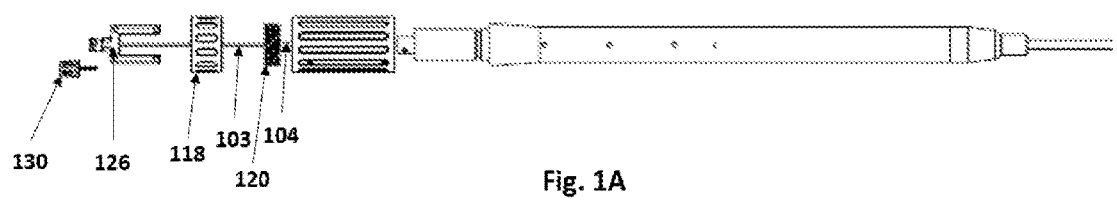
FIG. 1A illustrates a side, blow-up view of a secondary rotary knob of a transcatheter system for implant delivery, according to certain example embodiments.

Referring to FIGS. 1 and 1A, according to an embodiment of the present disclosure of the catheter system for implant delivery (100). The catheter system for implant delivery (100) comprises a distal section (400), a middle section (300), and a proximal section (200). The proximal end (200) remains outside the body of the living entity and comprises a handle (110) that encompasses mechanisms to control the movements at the distal end of the catheter inside a handle housing (112). The distal section (400) comprises a tip (101), a capsule (102) which is the distal part of a catheter shaft (106), an implant holder (109) which is connected at the distal end of the inner shaft (104), and a portion of the guidewire shaft (103) where an implant (not shown in figures) is housed.

The middle section (300) is situated between the handle (110) and an implant holder (109). The middle section (300) comprises at least an inner shaft (104), a guidewire shaft (103) and the catheter shaft (106). All the shafts are arranged concentrically i.e., over the length of the middle section at a point where all shafts are present, cross sectionally. The shafts are arranged, from the center; in the following order: the guidewire shaft (103), the inner shaft (104), and the catheter shaft (106).

The proximal section (200) comprises the handle (110) that comprises a primary rotary knob (116) and a secondary rotary knob (118). Both the knobs (116 and 118) are fixed longitudinally but both the knobs are rotatable on their axis. Rotary movement of the primary rotary knob (116) causes longitudinal movement of the catheter shaft (106) from the implant holder (109) till the tip (101) and thus loads or unloads the implant that is housed on a portion of the guidewire (103) and between the implant holder (109) and the tip (101). Both, the primary rotary knob (116) and the secondary rotary knob (118), are situated in a handle housing (112).

Figure 2:
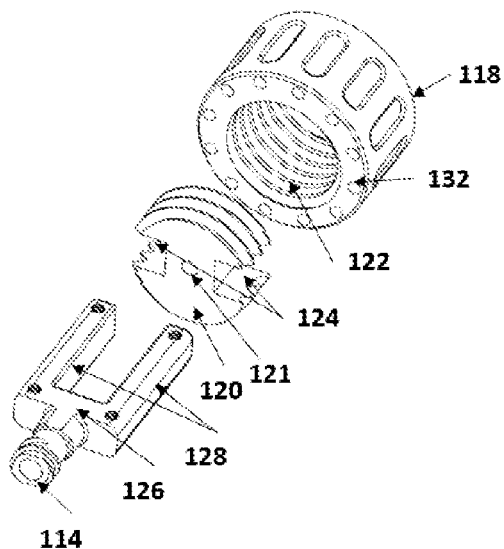
FIG. 2 illustrates an isometric, blow-up view of different parts used in assembling the secondary rotary knob of the transcatheter system for implant delivery (safety pin is not shown here), according to certain example embodiments.
Figure 2A:
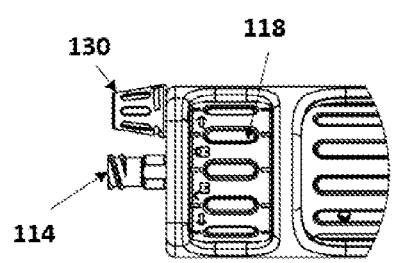
FIG. 2A illustrates a side view of the secondary rotary knob of the transcatheter system for implant delivery, according to certain example embodiments.
Figure 2B:
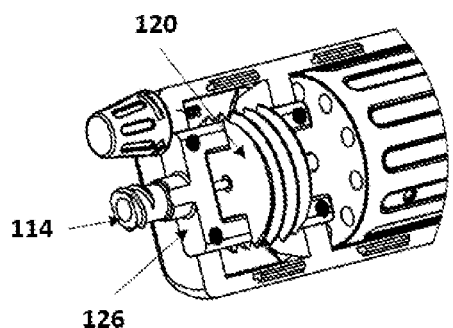
FIG. 2B illustrates an isotropic view of the secondary rotary knob of the transcatheter system for implant delivery, according to certain example embodiments.
Figure 3:
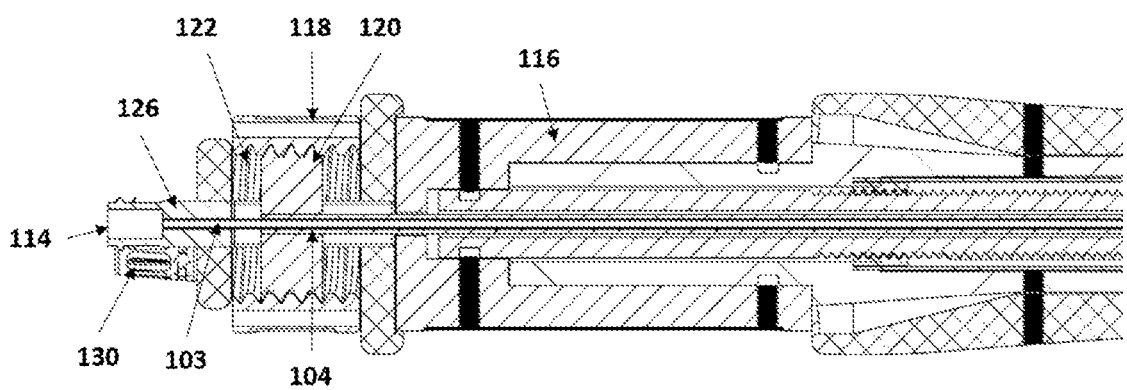
FIG. 3 illustrates a side, cross-sectional view of the secondary rotary knob of the transcatheter system for implant delivery, according to certain example embodiments.

Referring to FIGS. 2, 2A, 2B, and 3 according to an embodiment of the present disclosure of the catheter system for implant delivery (100). The secondary rotary knob (118) has inner threads (122) which are engaged with the threaded wheel (120) through threads on its outer periphery. The threaded wheel (120) has two grooves (124) cut in a longitudinal direction and that engage to the eccentric luer (126) through the grooves (124). Two luer arms (128) of the eccentric luer (126) goes through the grooves (124)—e.g., as shown in FIG. 2B.

The threaded wheel (120) also has a narrow hole (121), which is located on the cross-sectional surface of the threaded wheel (120), that engages with the proximal end of the inner shaft (104) (e.g., the inner shaft 104 slots into narrow hole 121). Further, the eccentric luer (126) also has a guidewire port (114) that engages with (e.g., is connected with) the guidewire shaft (103). The luer arms (128) function as a guiderail for the threaded wheel (120) for its movement over the luer arms (128) in longitudinal direction.

Rotary movement of the secondary rotary knob (118) causes movement of the threaded wheel (120) in longitudinal direction and the inner shaft (104) also moves accordingly in longitudinal direction. The guidewire shaft (103) is fixed to the eccentric luer (126) and remains stationary.

Hence, on rotating the primary rotary knob (116), macro movement takes place, and the housed implant is uncovered for deployment. Rotation of the secondary rotary knob (118) causes micro movement, such as, for example, that allows for better positioning of the implant and/or ensuring detachment of the implant from the implant holder due to movement of the implant holder in longitudinal direction.

In addition, the secondary rotary knob (118) comprises a safety pin (130) that engages with one of one or more safety slots (132) present on the cross-sectional of the secondary rotary knob (11) to restrict the unwanted movement of the secondary rotary knob (118). In some examples, plural such safety slots (e.g., as shown in FIG. 2B) may be disposed within the cross-sectional of the secondary rotary knob (11).

In the above description, for purpose of explanation, specific details are set forth in order to provide an understanding of the present disclosure. It will be apparent, however, to one skilled in the art that other embodiments may be practiced apart from the specific details described herein. One skilled in the art will recognize that embodiments of the present disclosure, one of which is described herein, may be incorporated into a number of systems. Further, structures and devices shown in the figures are illustrative of certain exemplary embodiments of the present disclosure and are meant to avoid obscuring the present disclosure with unnecessary detail.

| List of Reference Numerals | |
|---|---|
| Numeral Reference | Element Name |
| 100 | Catheter system for implant delivery |
| 102 | Capsule |
| 101 | Tip |
| 104 | Inner shaft |
| 106 | Catheter Shaft |
| 103 | Guidewire shaft |
| 109 | Implant holder |
| 110 | Handle |
| 112 | Handle housing |
| 114 | Guidewire Port |
| 116 | Primary rotary knob |
| 118 | Secondary rotary knob |
| 120 | Threaded wheel |
| 121 | Narrow hole |
| 122 | Internal threads |
| 124 | Groove |
| 126 | Eccentric luer |
| 128 | Luer arm |
| 130 | Safety pin |
| 132 | Safety slot |
| 200 | Proximal section |
| 300 | Middle section |
| 400 | Distal section |

We claim:

1. A percutaneous catheter for delivery of an implant, comprising:
   a primary rotary knob connected with a catheter shaft to facilitate longitudinal movement of the catheter shaft;
   a secondary rotary knob connected with an inner shaft to facilitate longitudinal movement of the inner shaft, the secondary rotary knob connected to a threaded wheel, the threaded wheel engaged with the secondary rotary knob through threads;
   an eccentric luer having a guidewire port connected to a guidewire shaft;
   at least one luer arm connected to the eccentric luer, the at least one luer arm positioned so that a longitudinal axis of the at least one luer arm is parallel to, but radially distant from, a longitudinal axis that passes through a center of the guidewire port and the guidewire shaft; and
   at least one groove that is cut into the threaded wheel, the at least one groove being accessible from at least one cross-sectional surface of the threaded wheel,
   wherein the at least one luer arm is configured to pass through the at least one groove in the threaded wheel, and the threaded wheel is configured to move in a longitudinal direction over the at least one luer arm based on rotary motion of the secondary rotary knob.

2. The percutaneous catheter for implant delivery as claimed in claim 1, wherein the threaded wheel comprises a narrow hole into which the inner shaft is slotted.

3. The percutaneous catheter for implant delivery as claimed in claim 2, wherein an additional element is present between an inner periphery of the narrow hole and an outer periphery of the inner shaft.

4. The percutaneous catheter for implant delivery as claimed in claim 3, wherein a physical shape of the additional element is selected from a hollow circular ring, a hollow cylinder, a ring whose periphery, inner or outer, has at least one angle, a ring whose periphery, inner or outer, has threads, a ring whose periphery, inner or outer, has at least one barb or a combination thereof.

5. The percutaneous catheter for implant delivery as claimed in claim 1, wherein an additional element is present between an inner periphery of the guidewire port and an outer periphery of the guidewire shaft.

6. The percutaneous catheter for implant delivery as claimed in claim 5, wherein the additional element is connected to different elements through adhesive, sealant, glue, threads, welding or a combination of thereof.

7. The percutaneous catheter for implant delivery as claimed in claim 5, wherein material of the additional element is selected from metal, non-metal, alloy, polymer, wood, natural fiber, synthetic fiber or a combination thereof.

8. The percutaneous catheter for implant delivery as claimed in claim 5, wherein a physical shape of the additional element is selected from a hollow circular ring, a hollow cylinder, a ring whose periphery, inner or outer, has at least one angle, a ring whose periphery, inner or outer, has threads, a ring whose periphery, inner or outer, has at least one barb or a combination thereof.

9. The percutaneous catheter for implant delivery as claimed in claim 1 comprises a safety mechanism to lock movement of the secondary rotary knob.

10. The percutaneous catheter for implant delivery as claimed in claim 9, wherein the safety mechanism comprises a safety pin and a safety slot wherein the safety pin and the safety slot, when engaged, lock the movement of the secondary rotary knob.

11. The percutaneous catheter for implant delivery as claimed in claim 9, wherein the safety mechanism is selected from threaded type, hook type, lock-pin type, switch type, Velcro-based, magnetic type or a combination thereof.

12. The percutaneous catheter for implant delivery as claimed in claim 1, wherein the implant is selected from a stent, a valve, a mesh, a balloon, a patch, a drug-containing matrix, a shunt, a vena cava filter, a vascular graft, a stent graft or a combination thereof.

13. The percutaneous catheter for implant delivery as claimed in claim 1, comprises an indicating mechanism to show extent of the implant delivery.

14. The percutaneous catheter for implant delivery as claimed in claim 1, further comprises at least one radiopaque marker on a peripheral surface of components selected from a tip, a capsule, the guidewire shaft, or a combination thereof.

* * * * *